(12) United States Patent
de Bevilacqua et al.

(10) Patent No.: US 11,896,727 B2
(45) Date of Patent: Feb. 13, 2024

(54) LIGHTING AND SANITIZATION DEVICE

(71) Applicant: ARTEMIDE S.p.A., Milan (IT)

(72) Inventors: Carlotta Francesca Isolina Maria de Bevilacqua, Milan (IT); Fabio Zanola, Missaglia (IT)

(73) Assignee: ARTEMIDE S.P.A.

( * ) Notice: Subject to any disclaimer, the term of this patent is extended or adjusted under 35 U.S.C. 154(b) by 334 days.

(21) Appl. No.: 17/313,167

(22) Filed: May 6, 2021

(65) Prior Publication Data
US 2021/0346546 A1 Nov. 11, 2021

(30) Foreign Application Priority Data

May 8, 2020 (IT) .................... 102020000010399

(51) Int. Cl.
*A61L 2/10* (2006.01)
*A61L 2/08* (2006.01)

(52) U.S. Cl.
CPC .................. *A61L 2/10* (2013.01); *A61L 2/084* (2013.01); *A61L 2202/11* (2013.01); *A61L 2202/14* (2013.01)

(58) Field of Classification Search
CPC ........ A61L 2/10; A61L 2/084; A61L 2202/11; A61L 2202/14; A61L 9/18; A61L 2202/25; A61L 2209/11; A61L 2209/12; F21Y 2113/10; F21Y 2115/10; F21V 23/003; F21V 33/0064
See application file for complete search history.

(56) References Cited

U.S. PATENT DOCUMENTS

| | | | |
|---|---|---|---|
| 9,439,989 B2* | 9/2016 | Lalicki | A01K 29/00 |
| 9,927,097 B2* | 3/2018 | Lalicki | H01L 33/502 |
| 10,413,626 B1* | 9/2019 | Barron | A61N 5/0624 |
| 2016/0030610 A1 | 2/2016 | Peterson | |
| 2020/0093944 A1* | 3/2020 | Yamada | H05B 47/16 |
| 2020/0242322 A1* | 7/2020 | Weaver | H04N 25/40 |

FOREIGN PATENT DOCUMENTS

| | | |
|---|---|---|
| CN | 202419518 | 9/2012 |
| WO | WO 2017/179082 | 10/2017 |

* cited by examiner

*Primary Examiner* — Bao Q Truong
(74) *Attorney, Agent, or Firm* — The Belles Group, P.C.

(57) ABSTRACT

A lighting and sanitization device, comprises: a first light source emitting violet light having a wavelength between 380 and 430 nm; a second light source emitting white light; a third light source emitting lime light having a peak wavelength between 535 and 545 nm.

10 Claims, 9 Drawing Sheets

LIGHTING AND SANITIZATION DEVICE

CROSS-REFERENCE TO RELATED APPLICATIONS

This Patent Application claims priority from Italian Patent Application No. 102020000010399 filed on May 8, 2020, the entire disclosure of which is incorporated herein by reference.

TECHNICAL FIELD

The present invention relates to a lighting and sanitization device, which integrates the normal environment lighting function with a sanitizing (disinfectant, antibacterial, etc.) function, capable of deactivating or eliminating pathogenic microorganisms.

BACKGROUND ART

It is known to use UV lamps with disinfectant function, since UV light is capable of deactivating or eliminating pathogenic microorganisms.

On the other hand, UV light is not suitable for lighting environments and also has potentially dangerous effects on humans too, if not properly controlled.

It is also known that certain light radiations in the visible range, particularly in the violet range, can have disinfectant effects.

For example, U.S. Pat. No. 9,439,989 discloses a lighting device comprising a first light source which emits radiation with a wavelength between 380 nm and 420 nm and has antibacterial function; and a second light source which emits radiation of a different wavelength from the first light source and such that the combination of the light emitted by the two sources generates a white light, which can therefore also be used for lighting the environment.

Further examples of this type of lighting devices, which use a light source emitting specific-wavelength violet light with disinfectant function combined with a light source emitting a complementary light resulting in white light, are described in U.S. Pat. Nos. 9,927,097 and 10,413,626.

The known lighting devices described above, in which the white light performing the lighting function originates from the combination of light emitted by the violet source and a specially designed source, may not be fully satisfactory as regards simplicity of construction and photometric performance, particularly visual comfort, and especially in cases where it is necessary to comply with lighting standards and regulations, for example in the workplace.

DISCLOSURE OF INVENTION

It is an object of the present invention to provide a lighting device which allows the drawbacks of the prior art described herein to be overcome; in particular, it is an object of the invention to provide a lighting device which is particularly efficient, functional, and versatile.

Therefore, the present invention relates to a lighting device as defined essentially in the appended claim 1 and, in its additional features, in the dependent claims.

The lighting and sanitization device of the invention is simple, efficient, functional, and versatile, being able to provide both effective lighting of the environment and effective sanitization against pathogenic microorganisms.

BRIEF DESCRIPTION OF THE DRAWINGS

Further features and advantages of the present invention will be apparent from the following description of a non-limiting embodiment thereof, with reference to the accompanying drawings, wherein.

BEST MODE FOR CARRYING OUT THE INVENTION

Figure 1:
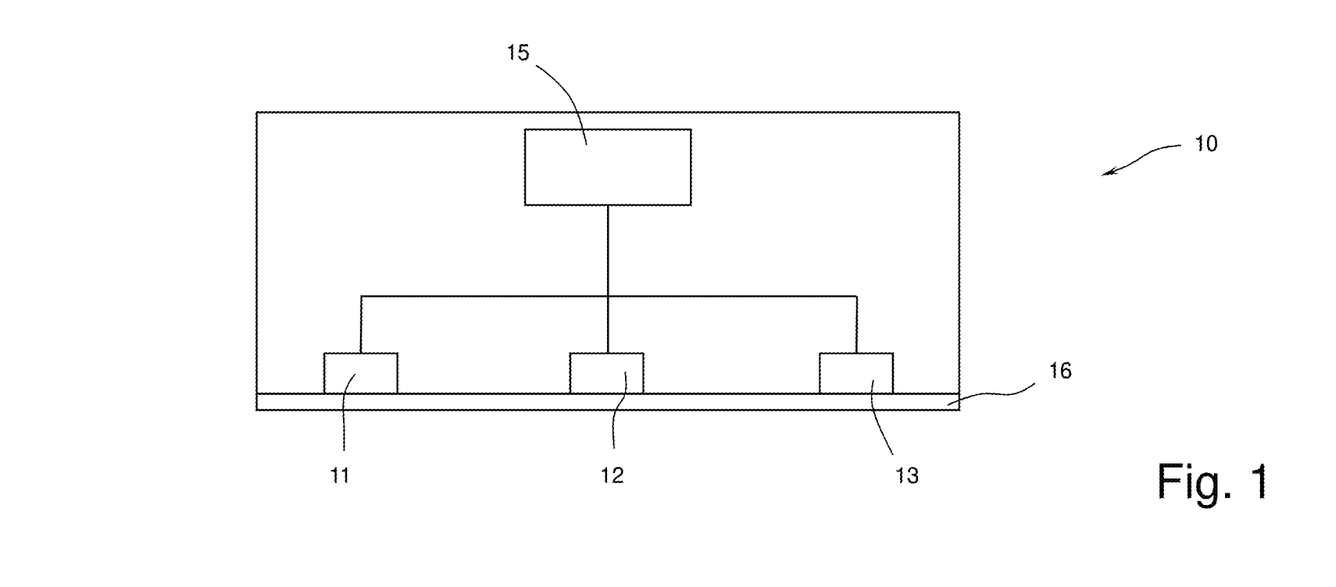
FIG. 1 is a schematic view of a lighting device according to a first embodiment of the invention.

Number 10 in FIG. 1 indicates a lighting device as a whole, that is, intended for lighting environments (in particular, but not only, indoor environments).

The device 10 comprises:
a first light source 11 emitting violet light;
a second light source 12 emitting white light;
a third light source 13 emitting lime light (yellow-green).

The device 10 further comprises a control unit 15 operatively connected to the sources 11, 12, 13 for controlling the operation (switching on/off and adjusting the intensity) and optionally, an optical assembly 16 associated with the sources 11, 12, 13 for levelling the emission from the sources 11, 12, 13.

Preferably, the sources 11, 12, are LED light sources comprising one or more LEDs.

For example, each source 11, 12, 13 comprises a plurality of identical LEDs connected in series.

Figure 2:
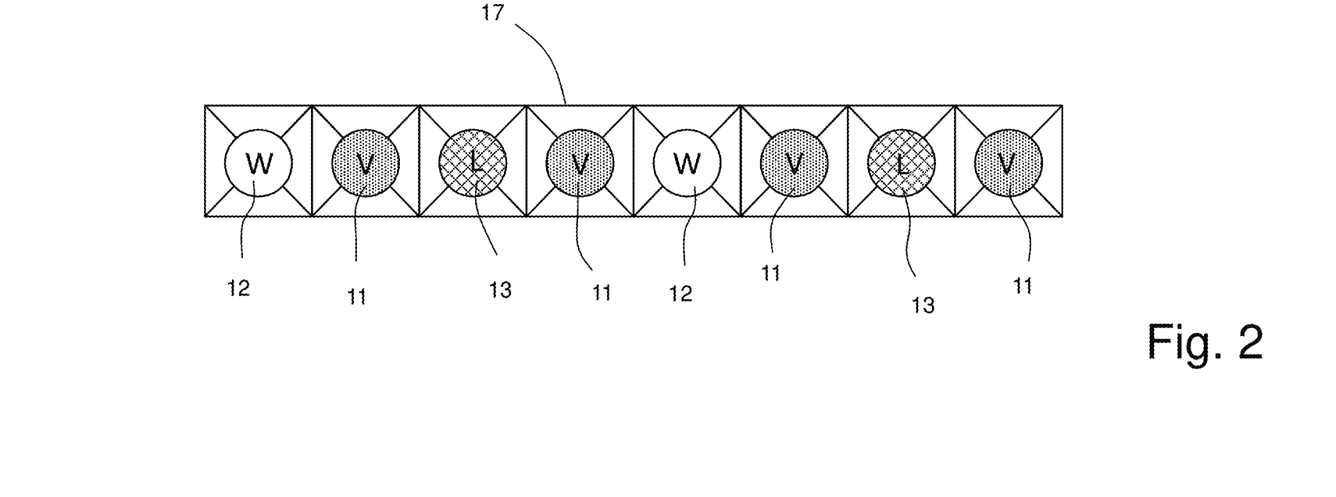
FIG. 2 is a schematic view of an LED board used in the device of FIG. 1.

In the non-limiting example in FIG. 2, the sources 11, 12, 13 are arranged on an LED board 17 having eight LEDs, namely: four violet-light LEDs (V) connected in series to define the source 11; two white light LEDs (W), connected in series to define the source 12; two lime-light LEDs (L), connected in series to define the source 13.

However, it is understood that the device 10 may include a different number of sources, organized according to different schemes, even on multiple LED boards.

The violet light source 11 emits light having a wavelength between 380 and 130 nm, in particular having a peak wavelength at 405 nm.

In particular, the white light source 12 consists of one or more white light LEDs having a color temperature ranging between 2800 and 3200 K, preferably between 2900 and 3100 K; and a color rendering index (CRI) ranging between 85 and 95, preferably equal to or greater than 90. In a preferred embodiment, the source 12 has a color temperature of 3000 K and a CRI of 90.

The lime light source 13 (yellow-green) emits lime light having a main peak at a wavelength between 535 and 545 nm; and a secondary peak at a wavelength between 435 and 440 nm.

The use of the lime light source 13 allows a greater energy contribution from the violet light source 11, which can result in shorter application times than a solution only providing a combination of white light and violet light. In fact, the antibacterial action is achieved by applying onto the exposed surfaces a certain irradiance value "I" (typically in the 380-430 nm band) expressed in mW/cm^2 for a time "t" expressed in seconds. The result of the product I×t, or more generally the result of the integral of the irradiance over time, is an energy density value, normally expressed in J/cm^2. The energy density value is what is then placed in relation to the doses that produce bacterial population reduction effects for all those families of bacteria and microorganisms in general that are sensitive to certain wavelengths.

By way of example, in a typical daytime mode operation (3500K white light with the maximum permissible violet component), the device 10 (mounted at an intended installation height) produces an irradiance (between 380 and 430 nm) on the worktable around 0.1 mW/cm^2.

In daytime use (typically 12 hours) the energy density value will be:

$$Qe = 0.1 \times (12 \times 3600) = 4.3 \text{ J/cm}^2.$$

The energy density level reached can be considered effective to reduce colony growth, at least of that portion of pathogenic bacteria most investigated by researchers and found to be sensitive to these radiations.

In night-time mode, with 100% violet light alone, the irradiance on the worktable can reach values of 1 and 2 mW/cm^2 and above depending on the configuration and location of the device 10 in the environment.

In this case, assuming a night-time use of 12 hours, the energy density reaches levels of about 80 J/cm^2, i.e., values sufficient to reduce the photosensitive bacterial colonies according to trajectories linked to the different families of bacteria with which one has to deal.

In a preferred embodiment, but not necessarily, the lime light source 13, according to the CIE 1931 diagram, has the following color coordinates:

$$x = 0.405$$

$$y = 0.540$$

The use of said source enables a higher percentage of violet light than a traditional white-violet system, since the lime color is opposite the violet color in the color diagram.

Since, in the daytime mode, the goal is to have a resultant on the black body curve, the violet light needs to have a higher power to contrast the color of the white lime mix that is located in the white-green region.

Figure 3:
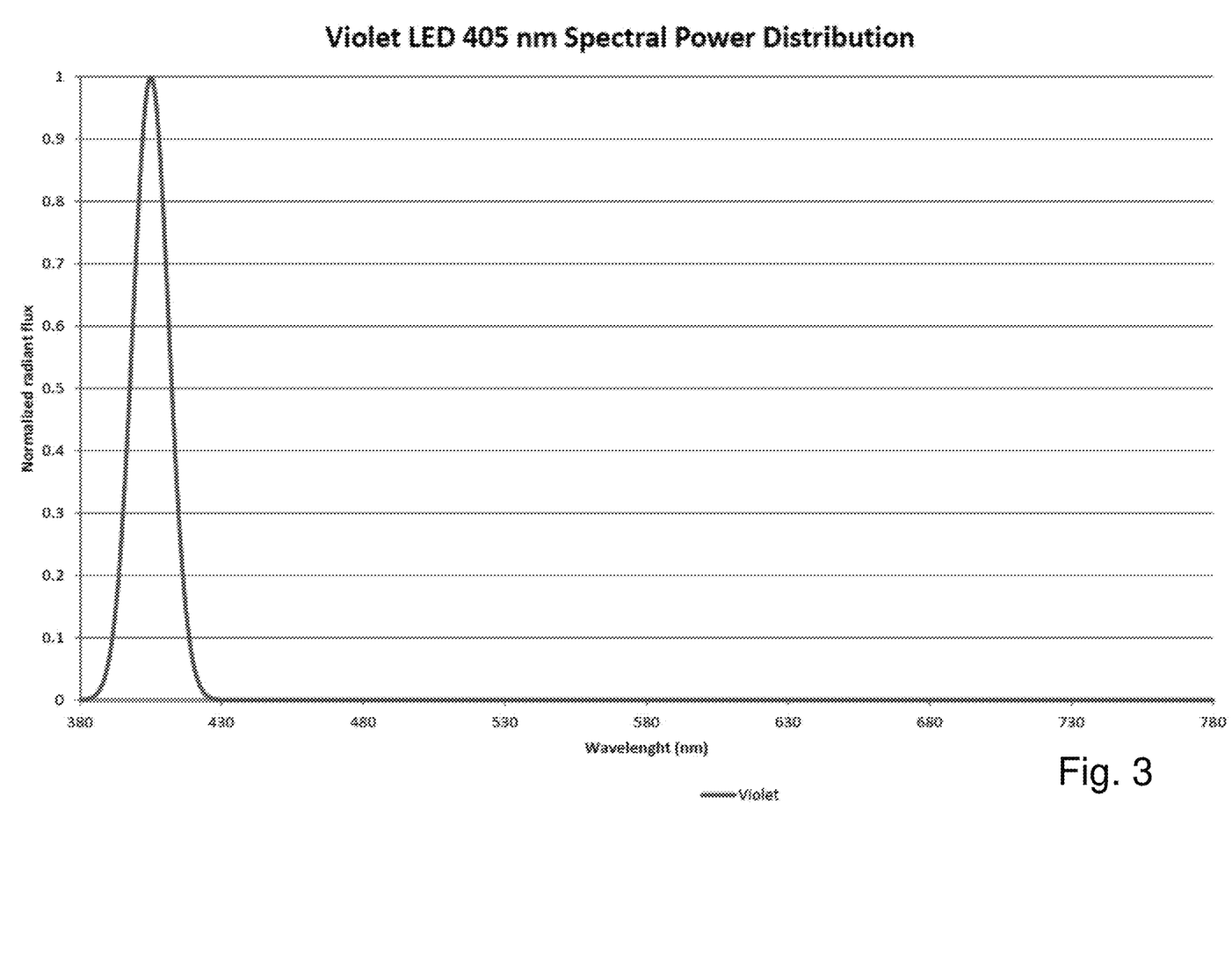
FIG. 3 is a graph showing the Spectral Power Distribution (SPD) of a first light source used in the device of FIG. 1.
Figure 4:
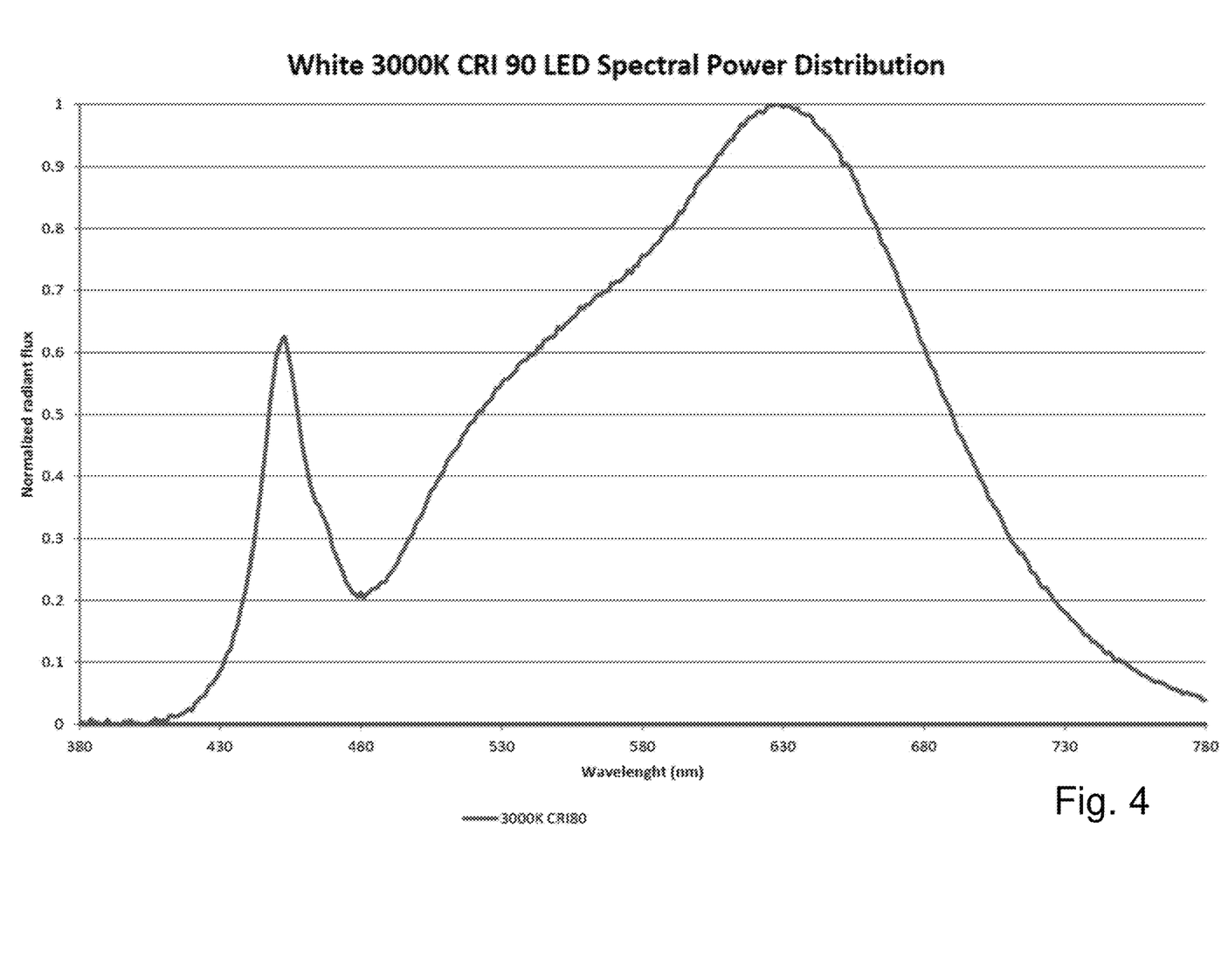
FIG. 4 is a graph showing the Spectral Power Distribution (SPD) of a second light source used in the device of FIG. 1.
Figure 5:
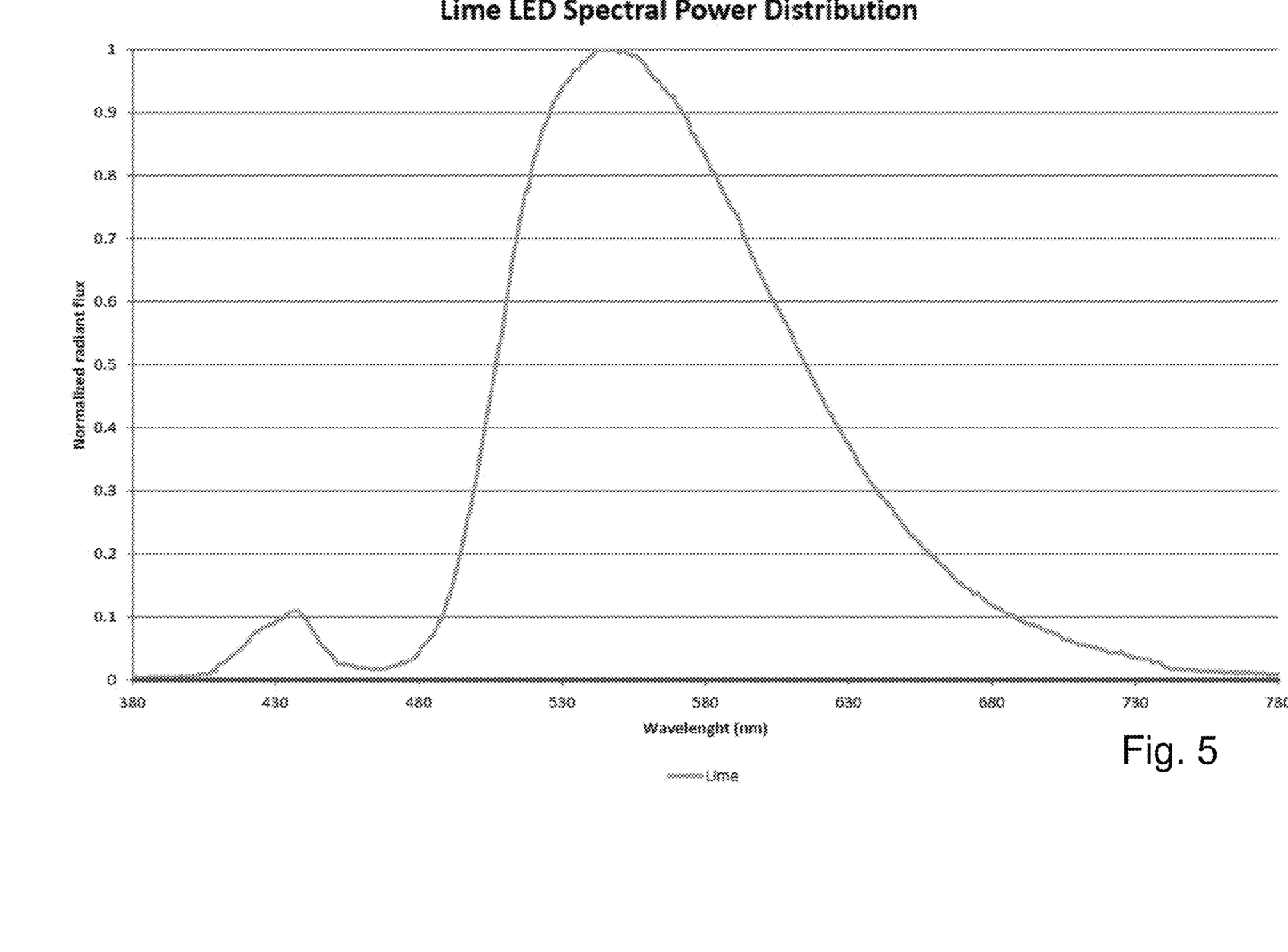
FIG. 5 is a graph showing the Spectral Power Distribution (SPD) of a third light source used in the device of FIG. 1.

In a preferred embodiment, the sources 11, 12, 13 are characterized by spectral power distributions shown in the graphs of FIGS. 3, 4 and 5, respectively (which show the wavelength on the abscissa and the normalized radiant flux of the respective light source on the ordinate).

The lime light source 13 has the purpose of balancing in the color space the effect induced by the violet light emitted by the violet light source 11, having a disinfectant function, on the color coordinate of the white light emitted by the white light source 12.

In this way, the light emission from the device 1 is perceived by the observers as white light, despite the presence of the violet component.

Figure 6:
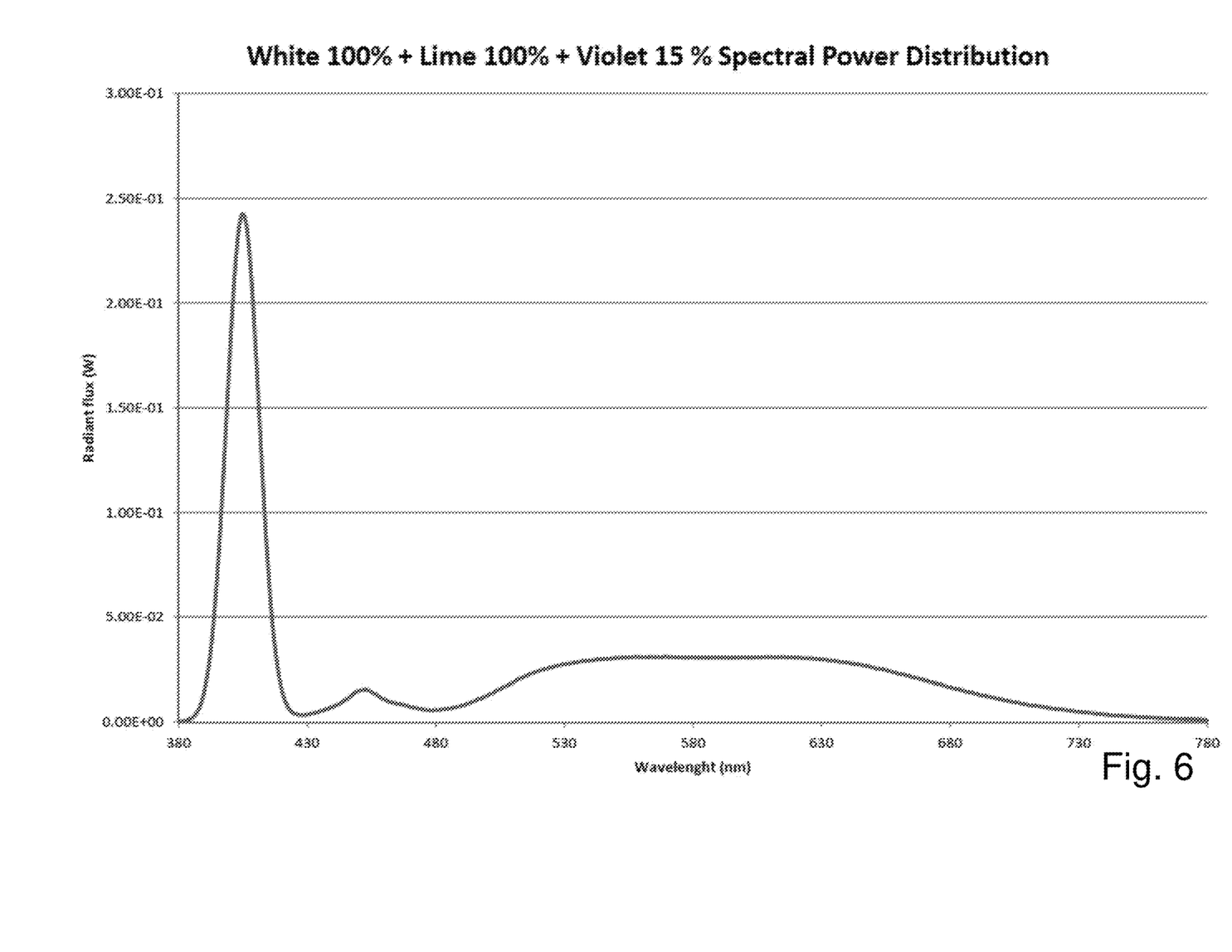
FIG. 6 is a graph showing the Spectral Power Distribution (SPD) of the device of FIG. 1.

FIG. 6 shows the graph of the spectral power distribution of the device 10 in a first mode of operation, in which the device 10 operates in lighting mode, being able to light the environment in which it is located with white light while providing an effective sanitization function.

In this mode, the sources 11, 12, 13 are all active: if necessary (depending on the installed sources and their power), the control unit 15 controls a different percentage of activation of each source 11, 12, 13 so that the resulting light is white light.

Advantageously, the violet light source 11 is oversized with respect so the lighting requirement.

The device is therefore configured so as to operate—controlled by the control unit 15—in at least two operating modes:

a lighting mode, in which all the sources 11, 12, 13 are switched on so that the device 10 has an overall emission of white light, given by the combination of the emissions from the combined sources 11, 12, 13; in particular, in this mode, the sources 12, 13 are active at the maximum available performance, whereas the source 11 is only partially active, i.e., the control unit 15 actuates the source 11 so that the source 11 has a controlled emission equal to a fraction of the maximum emission available for the source 11;

a sanitizing mode, in which the source 11 is at the maximum available performance, i.e., the control unit 15 actuates the source 11 so that the source 11 has an emission equal to the maximum available emission for the source 11; the sources 12, 13 can be switched on or off, depending on the requirements.

In the embodiment referred to in FIG. 6, with the sources indicated above by way of example, in the lighting mode, the sources 12, 13 are active a 100% of their power, whereas the source 11 is active at 15% of the available power.

Clearly, the percentage of activation of the sources 11, 12, 13 controlled by the control unit 15 so that the device 10 emits white light as a whole depends on the specific sources used and can vary with respect to what is described herein purely by way of example.

In any case, the control unit 15 is configured to selectively activate the sources 11, 12, 13 in a combined manner to provide an overall emission of white light.

Figure 7:
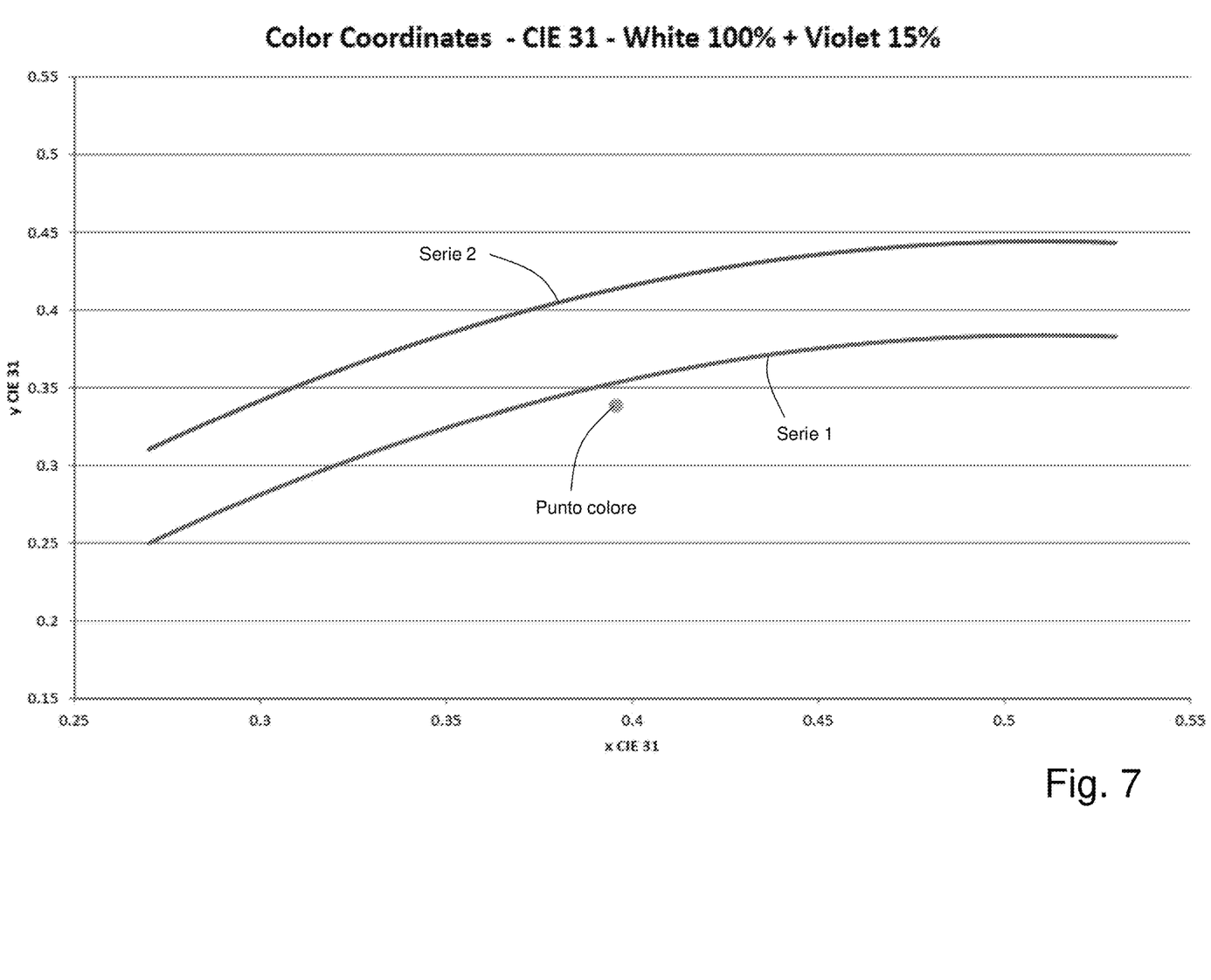
FIGS. 7 and 8 are graphs showing the color points of the lighting device in respective operating modes in the X, Y CIE 31 color coordinate plane.
Figure 8:
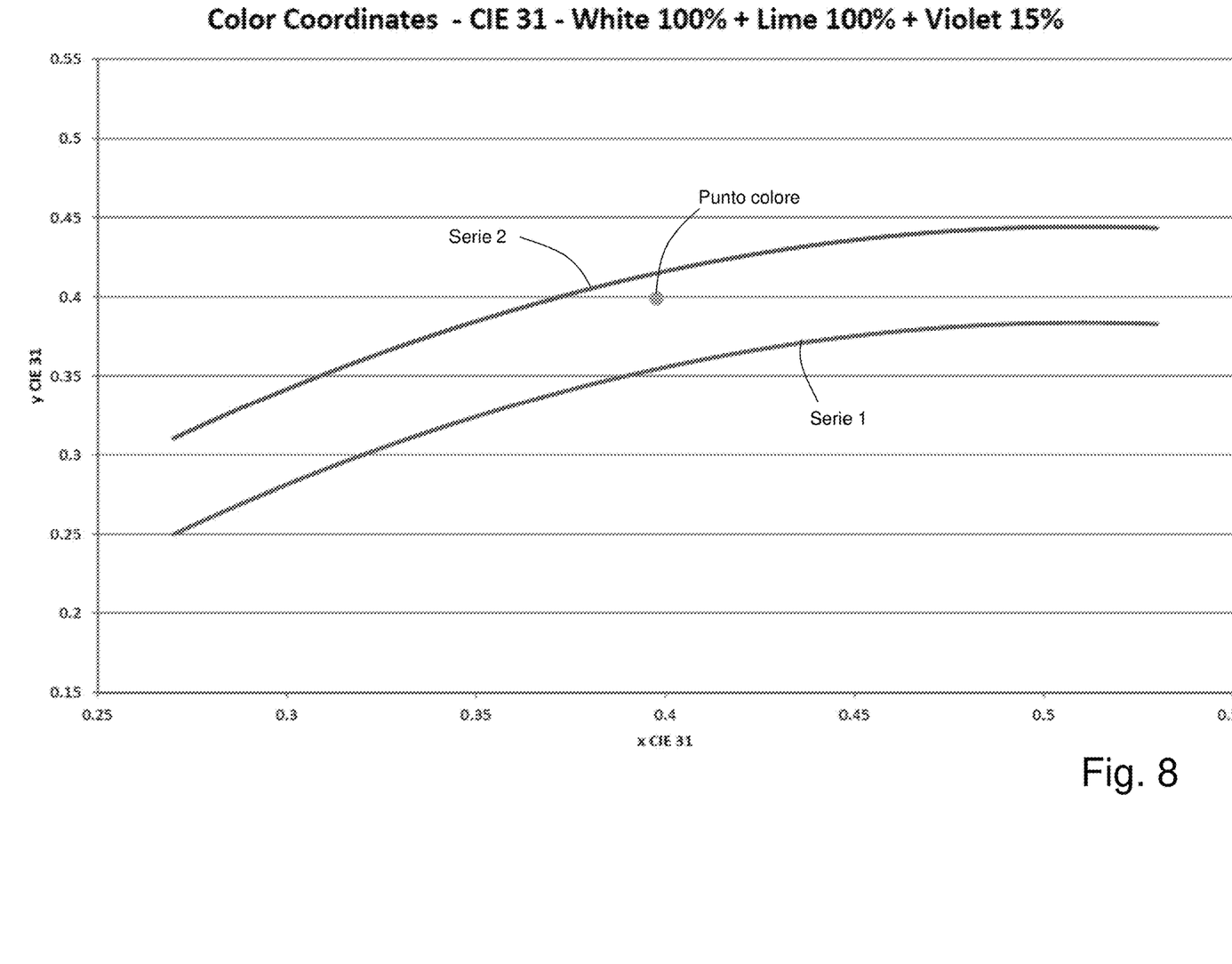

The effect is illustrated in the graphs of FIGS. 7 and 8, where two limit curves are shown on the X, Y CIE 31 color coordinate plane, respectively indicated as Series 1 and Series 2, corresponding to the color limits within which the color of the light emitted must fall in order to comply with the regulations in force for lighting devices.

FIG. 7 indicates the color point of the light emitted by the device 10, with the lime light source 13 off and the sources 11, 12 on: the color point is outside the limits provided.

Instead, FIG. 8 indicates the color point of the light emitted by the device 10, with the lime light source 13 on, together with the sources 11, 12: the color point is within the limits provided.

According to the invention, the presence of the lime light source 13 compensates for the violet light from source 11 so that the overall emission of the device 10 is perceived by the human eye as white light, and at the same time the device 10 provides a sanitizing effect induced by the violet light component.

Preferably, in order to improve the quality of the emitted light and also the overall efficiency of the device 10, a white light source 12 is selected, which has specific color temperature and spectrum characteristics (color rendering) and is capable of integrating the violet-lime component, and as a final result, to attain a white light of the desired quality. In fact, the balance provided by the lime light source 13 with respect to the light emitted by the violet light source 11 balances the energy and color aspects but may be insufficient to provide adequate light for the environment lighting requirements.

The relative weights of the sources 11, 12, 13 can also be varied and selected: it is possible to obtain the desired emission by varying the number of the sources 11, 12, 13 and their power supply currents.

From the electrical management point of view, the three sources 11, 12, 13 can be controlled by a two-channel system, where the sources 12 and 13 are managed by a first channel, and the violet light source 11 by a second channel).

It is understood that other configurations may be used, for example series-parallel solutions or high voltage solutions that may be specific to the characteristics of the violet LEDs, in particular, and their limited availability for electrical parameter selections.

On the other hand, in order to have the maximum possible sanitizing effect, the control unit 15 controls the sources 11, 12, so that the source 11 is 100% active, while the sources 12, 13 are off. Clearly, in this mode of operation, the device 10 does not provide suitable light for environment lighting.

The sole sanitization mode can be provided, for example, in the absence of people in the environment where the device 10 is installed.

For this purpose, in addition to a manual control operated by a user, the device 10 can be equipped with or connected to one or more sensors, for example, presence sensors, capable of detecting whether there are people in the environment where the device 10 is located and communicating the detection to the control unit 15, which adjusts the operating modes of the device 10 accordingly.

Generally, the control unit 15 is configured so as to selectively activate the sources 11, 12, 13, also independently from one another, and optionally to further adjust the light intensity and/or emitting power of each source.

In this way, for example, the device 10 can be operated in the lighting mode with a sanitizing function (with all the sources 11, 12, 13 switched on); or in the sanitizing mode alone (with the sole violet light source 11 switched on).

The control unit 15 is configured to activate the sources 11, 12, 13 according to a preset program, optionally including a time profile, so as to adjust the light emission of the device 10 according to different lighting requirements throughout the day and/or according to the place where the device 10 is installed; and/or according to signals received from sensors connected to the control unit 15.

The control unit 15 can also be configured so as to manage the transition from one operating mode to the other depending on the presence of people, until a daily dose is reached, in combination with sensors and programming. In particular, when the presence of people is detected, by means of presence sensors, the control unit 15 commands the switching on of the violet light source 11 so that its emission is within a predetermined threshold.

Figure 9:
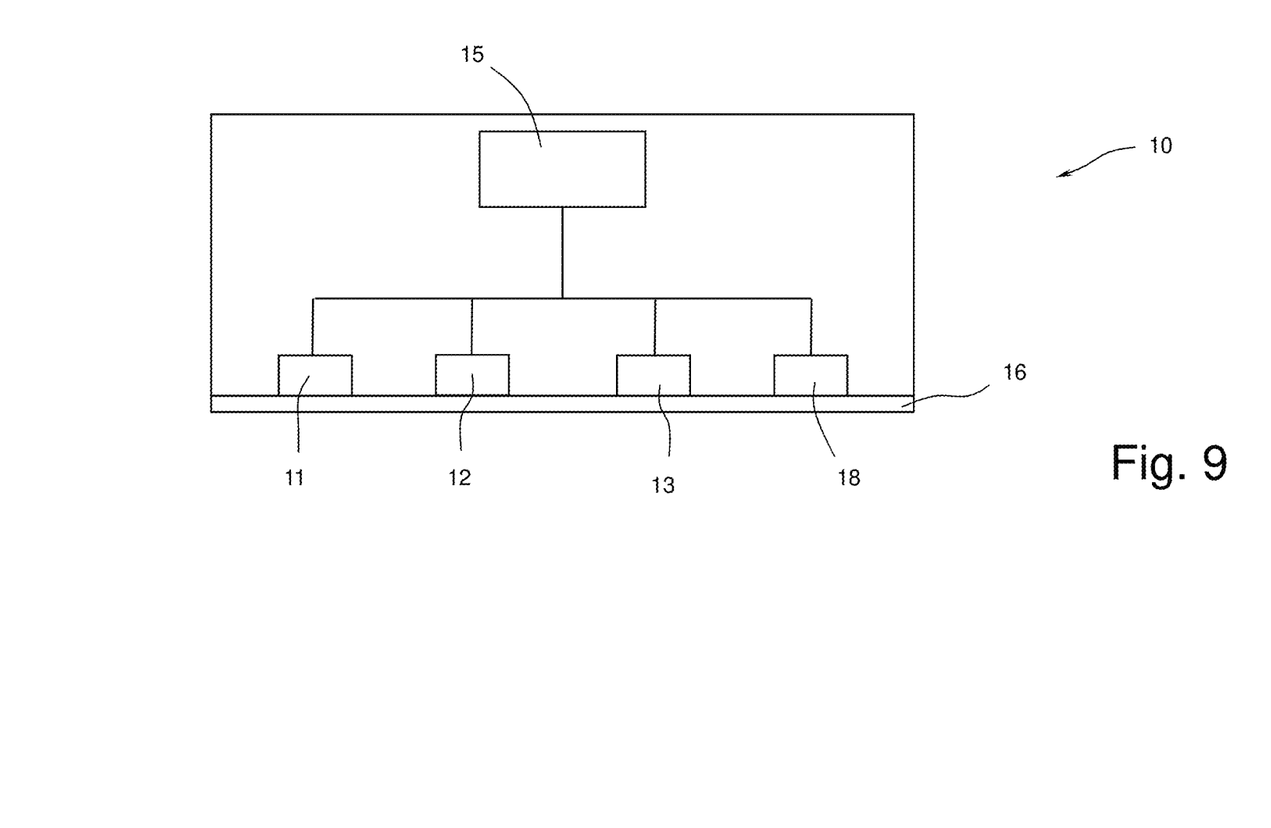
FIG. 9 is a schematic view of a lighting device according to a second embodiment of the invention.

In the embodiment of FIG. 9, the lighting device 10 further comprises a UV source 18, in particular a source emitting UV-C radiation, which replaces all or part of the violet light emitted by the violet light source 11.

Figure 10:
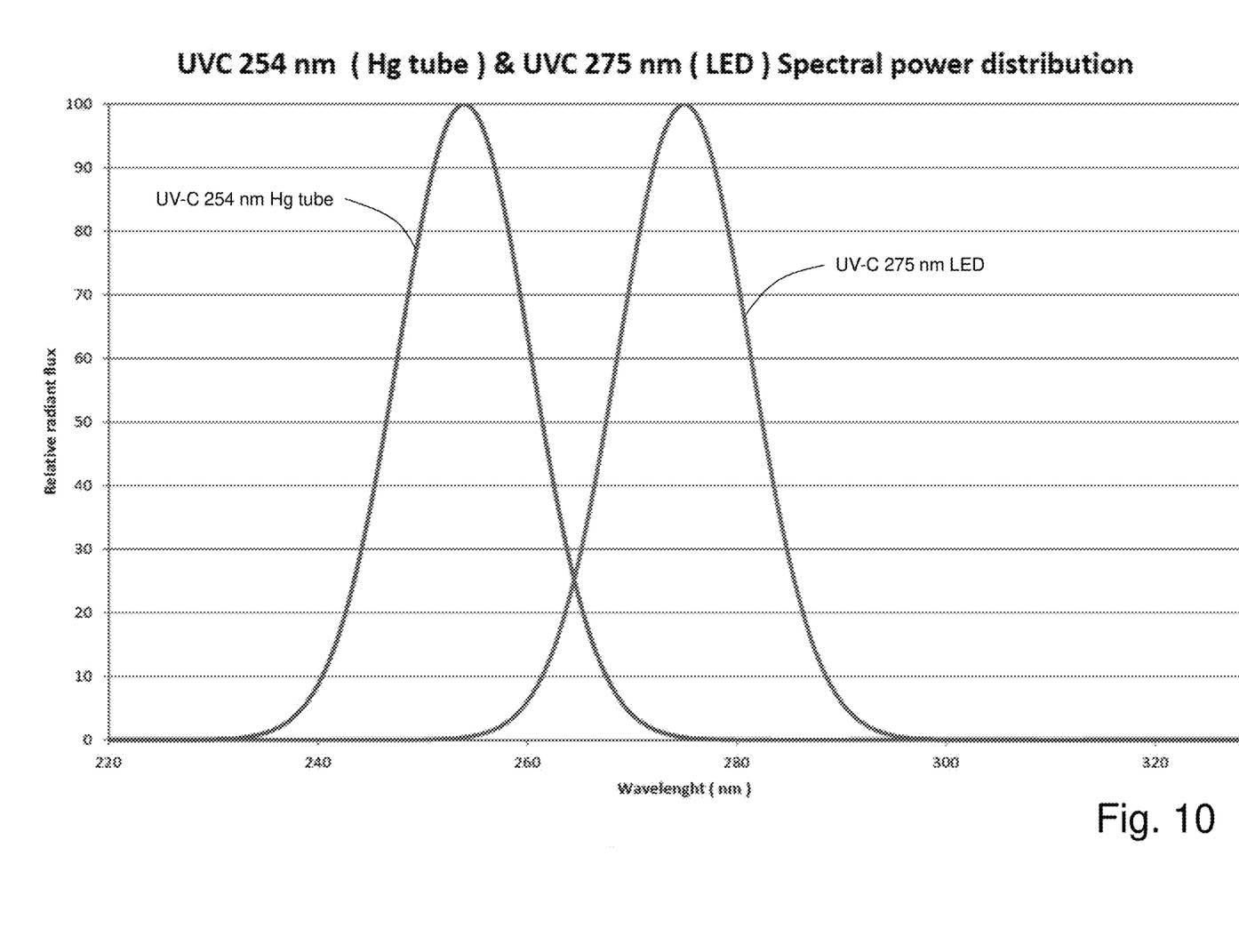
FIG. 10 is a graph showing the Spectral Power Distribution (SPD) of UV sources used in the device of FIG. 9.

For example, sources 18 may be used, which emit UV-C radiation with the spectral emission shown in FIG. 10. FIG. 10 shows the spectra (again in terms of spectral power distribution) of the UV-C radiation emitted by an LED source with a peak wavelength at 275 nm); and by a low-pressure mercury tubular source with a peak wavelength at 254 nm.

The control unit 15 of the device 10 is configured so as to selectively activate the violet light source 11 and/or the UV source 18, according to a preset program, optionally including a time profile, so as to take into account different lighting requirements throughout the day and/or according to the place where the device 10 is installed; and/or according to signals received from sensors (in particular, presence sensors detecting the presence of people in the lighted environment) connected to the control unit 15.

Conveniently, considering the greater potential danger of UV radiation to people, the activation of the UV source 18 is controlled by the control unit 15 based on the actual presence of people in the environment and/or for adequate and safe periods of time.

Optionally, the control unit 15 can be preset to activate the source 13 also based on the place where the device 10 is installed: if in the environment there are suitable materials and finishes and the space has dimensions suitable for the use of UV radiation, possibly for predetermined times.

As previously described, the activation of the UV source 18 can also be suitably controlled according to the signals received from sensors connected to the control unit 15, as well as on preset time profiles. In addition to presence detectors of various types, the control unit 15 can be connected to entry authorization systems and/or systems for detecting the presence of smart devices in the environment, or the like. Preferably, a redundancy of detection systems ensures correct operation of the UV sources in complete safety for people.

The control unit 15 controls the device 10 also to integrate the violet light source 11 and the UV source 18. In particular, if the use of the sole violet light generated by the source 11 is not fully effective in the sanitizing function, because the time available is not sufficient, for the violet light radiation to develop its action on micro-organisms, for example, then the control unit 15, in addition to the source 11, operates the UV source 18 too.

The control unit 15 allows the source 18 to be operated only if the conditions allow it and/or for a suitable period of time, always checking that conditions of safe use (presence of people, presence of suitable materials and finishes, sufficient spaces, etc.) are met.

The combined use of UV radiation, in particular UV-C, and violet light allows effective elimination of pathogens (ensured by UV radiation), whereas the violet light (compensated by the lime light) maintains a function of containment of bacterial regrowth, as well as contributing to functional lighting.

Lastly, it is understood that further modifications and variations can be made to the lighting device as described and illustrated herein without departing from the scope of the accompanying claims.

The invention claimed is:
1. A lighting and sanitization device, comprising:
   a first light source emitting violet light having a wavelength between 380 and 430 nm;
   a second light source emitting white light;
   a third light source emitting lime light having a peak wavelength between 535 and 545 nm; and
   a control unit operatively connected to the first light source, the second light source, and the third light source, the control unit configured to:

selectively activate one or more of: the first light source, the second light source, and the third light source independently from one another;

adjust the light intensity and/or emitting power of the first light source, the second light source, and the third light source; and activate the first light source, the second light source, and the third light source according to a preset program including a time profile to adjust the light emission of the device according to different lighting requirements throughout the day and/or according to a place where the device is installed and/or according to one or more signals received from one or more sensors connected to the control unit.

2. The device according to claim 1, wherein the first light source, the second light source, and the third light source are LED light sources, each comprising one or more LEDs.

3. The device according to claim 1, wherein the second light source, emitting white light, comprises one or more LEDs having a color temperature ranging between 2900 and 3100 K; and a color rendering index (CRI) equal to or greater than 90.

4. The device according to claim 1, wherein the third light source, emitting lime light, emits light which balances in the color space the effect induced by the violet light emitted by the first light source on the color coordinates of the white light emitted by the second light source, so as the combined light resulting from the combination of light emitted by all the first light source, the second light source, and the third light source is a white light.

5. The device according to claim 1, wherein the control unit is configured to control a different percentage of activation of each of the first light source, the second light source, and the third light source so that the resulting light is white light.

6. The device according to claim 1, further comprising a UV source emitting UV-C radiation, which can replace all or part of the violet light emitted by the first light source.

7. The device according to claim 6, wherein the control unit is configured to selectively activate the first light source, emitting violet light, and/or the UV source, according to a preset program including a time profile to adjust the light emission of the device according to different lighting requirements throughout the day, and/or according to a place where the device is installed, and/or according to one or more signals received from one or more sensors connected to the control unit.

8. The device according to claim 6, wherein the control unit is configured to activate simultaneously, for predetermined time periods and/or according to one or more signals received from one or more sensors, the first light source, emitting violet light, and the UV source.

9. The device according to claim 8, wherein the control unit is configured to:

activate together the first light source emitting violet light, and the UV source where the use of the violet light alone emitted by the first light source is not fully effective for sanitization; and allow the UV source to be activated only if the conditions allow it and/or for a suitable time period, always checking that conditions of safe use are met.

10. A lighting and sanitization device, comprising:
a first light source emitting violet light having a wavelength between 380 and 430 nm;
a second light source emitting white light;
a third light source emitting lime light having a peak wavelength between 535 and 545 nm;
a UV source emitting UV-C radiation, which can replace all or part of the violet light emitted by the first light source and
a control unit operatively connected to the first light source, the second light source, and the third light source, the control unit configured to:
selectively activate one or more of: the first light source, the second light source, and the third light source independently from one another;
adjust the light intensity and/or emitting power of the first light source, the second light source, and the third light source; and
selectively activate the first light source emitting violet light and/or the UV source according to a preset program including a time profile to adjust the light emission of the device according to different lighting requirements throughout the day, and/or according to a place where the device is installed, and/or according to one or more signals received from one or more sensors connected to the control unit.

* * * * *